United States Patent [19]
Chambost et al.

[11] Patent Number: 6,040,481
[45] Date of Patent: Mar. 21, 2000

[54] METHOD FOR HYDROGENATING AROMATIC NITRO COMPOUNDS

[75] Inventors: Bernard Chambost, Lyons; Philippe Marion, Villeurbanne; Corinne Mathieu, Lyons, all of France

[73] Assignee: Rhodia Chimie, Courbevoie, France

[21] Appl. No.: 09/077,637

[22] PCT Filed: Nov. 29, 1996

[86] PCT No.: PCT/FR96/01893

§ 371 Date: Nov. 12, 1998

§ 102(e) Date: Nov. 12, 1998

[87] PCT Pub. No.: WO97/20804

PCT Pub. Date: Jun. 12, 1997

[30] Foreign Application Priority Data

Dec. 1, 1995 [FR] France .................................. 95 14203

[51] Int. Cl.$^7$ .................................................. C07C 209/00
[52] U.S. Cl. ........................................... 564/422; 564/420
[58] Field of Search ..................................... 564/422, 420

[56] References Cited

U.S. PATENT DOCUMENTS 3,935,264  1/1976  Bhutani .................................... 564/422
5,877,350  3/1999  Langer et al. ........................... 564/423

Primary Examiner—Paul J. Killos
Assistant Examiner—Jatar Parsa
Attorney, Agent, or Firm—Jean-Louis Seugnet

[57] ABSTRACT

A method for hydrogenating aromatic nitro compounds by reacting at least one aromatic nitro compound with hydrogen in two adiabatically operated fixed-bed catalytic reactors arranged in series, wherein one part of the reaction mixture from the first reactor is recirculated therein while the other part is fed into the second reactor.

21 Claims, 1 Drawing Sheet

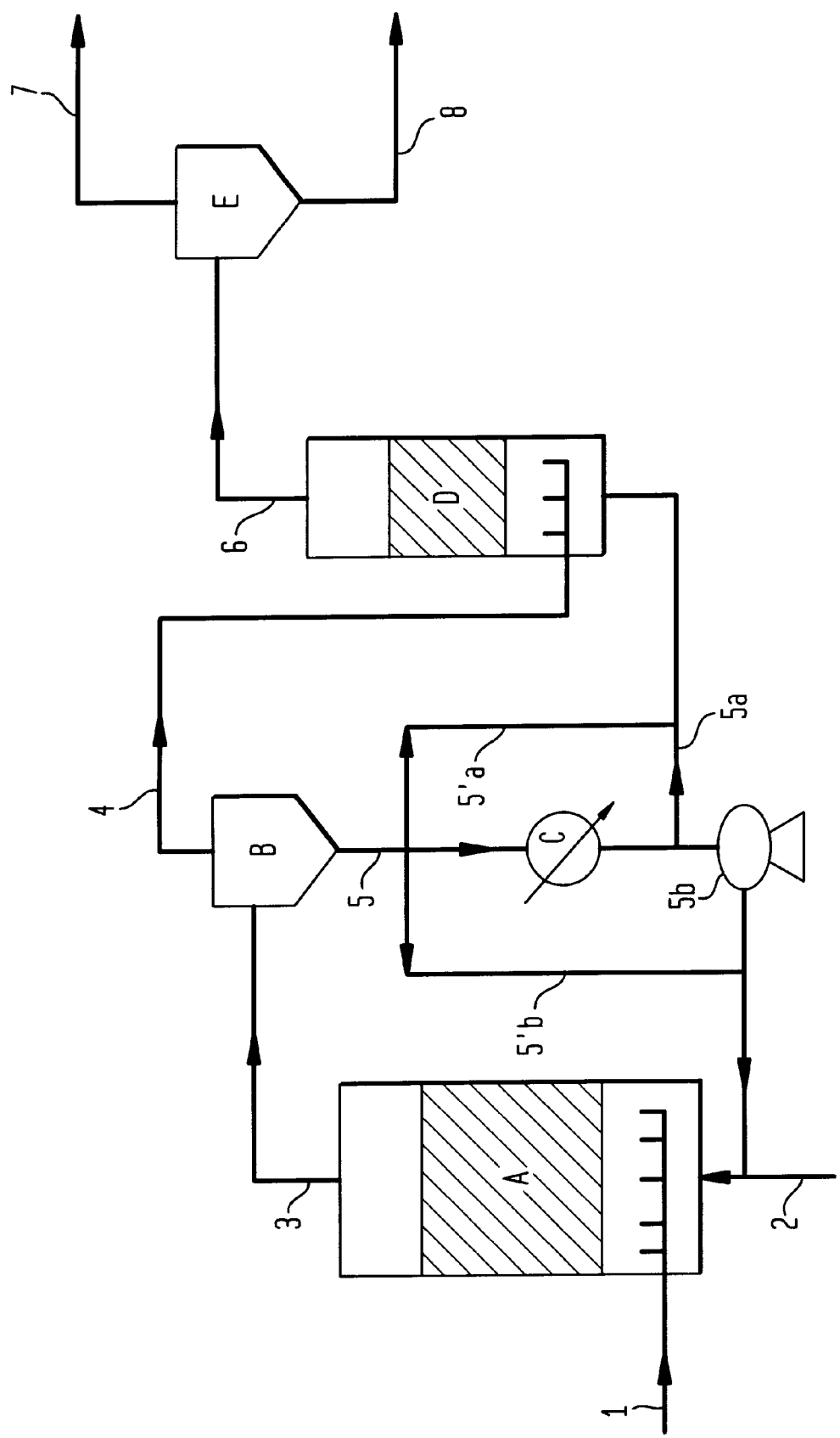

METHOD FOR HYDROGENATING AROMATIC NITRO COMPOUNDS

This application is an application under 35 U.S.C. Section 371 of International Application Number PCT/FR96/01893, filed on Nov. 29, 1996.

The present invention relates to the hydrogenation of aromatic nitro compounds using a catalyst in a fixed bed.

BRIEF DESCRIPTION OF DRAWING

Among the processes of this type, two categories can be listed, the first using a catalyst in the form of a stirred suspension, the second using a catalyst in a fixed bed.

Processes involving catalysts in the form of a stirred suspension have experienced considerable industrial developments. The reason for this is that, despite a large investment, they have the advantage of effectively controlling the exothermicity of the hydrogenation reaction, which is considerable for compounds of this type. Moreover, the hydrogenation of nitro compounds on a catalyst in a stirred suspension exhibits good performance, in terms of selectivity of desired compound, conversion of the nitro product and production efficiency. Lastly, the catalyst is relatively easy to replace for these processes, which contributes towards conserving their good performance.

The other category consisting in using catalysts in a fixed bed to hydrogenate aromatic nitro compounds has not experienced as extensive an industrial-scale development as the previous category. This is because the major difficulty with this process lies in the removal of the heat evolved during the reaction; if this removal of heat is not sufficient, it can lead to a runaway reaction, and also to a lowering in the performance of the process and degradation of the catalyst used.

One solution recommended to remove the heat of reaction has been to recycle a fraction of the reaction mixture, which has been cooled beforehand.

Thus, it has been proposed to hydrogenate aromatic nitro compounds in a tubular reactor with a fixed bed of flowing type (i.e. injection of the reactants co-currentwise downwards in the reactor) in which the supply flow comprises some of the recycled reaction mixture coming from the said reactor. However, the reactor dimensions are such that this reactor cannot be considered as operating adiabatically since 60 to 70% of the heat exchanges take place by means of losses through the walls of the said reactor. Consequently, extrapolation of this process to the industrial scale would result in having reactors whose height would be considerably greater than their cross-section, so as to conserve a reasonable level of heat exchange through the walls. However, such reactors would need to use very large amounts of catalyst, which would detract from one of the advantages of the process with a fixed bed compared with catalyst suspensions. Another possibility for the industrial-scale exploitation of this type of process would be to increase the heat exchanges with the recycled reaction flow. In other words, this would consist in increasing the rate of recycling of the reaction medium considerably. In this case, the production efficiency of such a process would be much too low, on account of the large dilution required for the compounds to be nitrated and the need to convert these compounds completely.

As may be observed, there is currently no process for the fixed-bed hydrogenation of aromatic nitro compounds which can be industrially exploited satisfactorily.

The subject of the present invention is thus to propose such a type of process, which does not have the abovementioned drawbacks of hydrogenation reactions using catalysts in a fixed bed.

Thus, the process according to the invention has all the advantages of processes using fixed beds when compared with processes using a stirred suspension of catalyst.

In particular, the process according to the invention is easy to carry out and incurs lower capital costs since it is no longer necessary to provide complex systems for separating out the catalyst once the reaction is complete, nor even to provide stirring systems, with all the problems of leaktightness inherent therein.

Furthermore, the process according to the invention allows the difficulties associated with carrying out the reaction in a fixed bed, i.e. the exothermicity of the reaction, to be solved.

Lastly, the performance levels of the process according to the invention, in terms of production efficiency and selectivity, are entirely comparable, in terms of production efficiency and selectivity, with those obtained by processes using stirred catalyst suspensions.

These aims and others are achieved by the present invention, the subject of which is thus a process for hydrogenating aromatic nitro compounds, in which at least one aromatic nitro compound is reacted with hydrogen in two fixed-bed catalytic reactors in series operating adiabatically; in this process, some of the reaction mixture leaving the first reactor is recycled into this reactor, the other part being introduced into the second reactor.

However, other characteristics and advantages of the present invention will become apparent on reading the description, the figure and the examples which follow.

For reasons of convenience, the apparatus units and their assembled sequence will first be described.

As has been mentioned previously, the process according to the invention is carried out in an assembly of two reactors in series.

Each of the reactors is preferably supplied co-currentwise with gas and liquid. It is possible to inject the reactants and/or the reaction mixture into the top or the bottom of the reactor.

In the first case, the process is in a so-called "flowing" catalytic bed and the continuous phase in the reactor is a gaseous phase.

According to a particularly advantageous and preferred embodiment of the invention, each of the reactors is supplied with hydrogen, at least one aromatic nitro compound and/or the recycled or non-recycled reaction mixture, co-currentwise, such that the continuous phase in the said reactors is liquid.

Such a result is obtained by supplying the reactors from the bottom upwards. In this way, the catalyst bed is immersed in the reactants and/or the reaction mixture.

This method of supply is particularly appropriate since it increases the efficiency of the gas-liquid and liquid-solid contacts. Moreover, the fact that the catalyst is continuously immersed reduces the risk of it degrading due to local overheating.

It would not constitute a departure from the context of the present invention if two reactors supplied differently were used. However, it is preferred to use two reactors supplied via the bottom.

One of the essential characteristics of the invention lies in the fact that some of the reaction mixture coming from the first reactor is recycled into the supply flow of this reactor, the other part being introduced into the second reactor.

More particularly, the ratio of the flow rate of supply of the first reactor with aromatic nitro compounds to the flow rate of reaction mixture recycled into the first reactor is such that the concentration of nitro compounds is between 0.1 and 10% by weight in the first reactor.

According to a specific embodiment of the invention, the ratio of the flow rate of supply of the first reactor with aromatic nitro compounds to the flow rate of reaction mixture recycled into the first reactor is between 5 and 1000.

The temperature at the foot of the first reactor is about 50 to 200° C. and more particularly about 80 to 170° C.

On leaving the first reactor, the rise in temperature, i.e. the difference between the outlet temperature of the reaction mixture and the inlet temperature of the nitro compounds and/or of the recycled reaction mixture, is less than 120° C.

The mixture leaving the first reactor comprises unreacted nitro compounds, the corresponding hydrogenated aromatic compounds, water and hydrogen.

According to one variant of the invention, the reaction mixture coming from the first reactor is introduced into a gas-liquid separator.

The resulting gaseous fraction is fed into the second reactor, whereas the liquid fraction is separated into two parts, one of which is recycled into the supply flow of the first reactor.

This separation operation can be carried out in any conventional type of apparatus, such as cylindrical tanks or cyclones.

Prior to the recycling in the first reactor, the reaction mixture is cooled in order to have the desired temperature after mixing with the reactants.

Preferably, the reaction mixture leaving the first reactor is separated from the gases it contains, prior to being recycled into this reactor and introduced into the second reactor.

Moreover, according to a specific embodiment of the invention, the reaction mixture introduced into the above-mentioned exchanger is a reaction mixture which has been freed of most of the gases it contains.

The reactors in which the process is carried out are preferably cylindrical tubes fitted with standard means for retaining the fixed bed of catalyst and for distributing the liquid and gas flows.

As may be observed, the reactors used are of simple and inexpensive technology, which represents an advantage over reactors with a suspension of stirred catalyst.

On account of the high level of recycling, the behaviour of the first reactor is of the stirred type.

As regards the second reactor, a piston-type reactor is used. It is advantageous to combine the two reactors since this makes it possible to minimize the overall amount of catalyst and thus the size of the reactors.

The size of these apparatus units can be determined in a conventional manner by those skilled in the art depending on the type of reactor (stirred, piston), the desired conversion and the flow rate of nitro compounds to be hydrogenated.

Most of the hydrogenation reaction is carried out in the first reactor. A degree of conversion of greater than or equal to 90% of hydrogenated aromatic nitro compounds relative to the aromatic nitro compounds fed into the recycling loop is achieved.

The second reactor corresponds to a finisher by means of which degrees of conversion of 100% are achieved.

Aromatic nitro compounds processed according to the process of the invention comprise at least one nitro group.

More particularly, the processed aromatic nitro compounds comprise at least two nitro groups.

As aromatic nitro compounds which are particularly suitable for the invention, mention may be made of nitrobenzene, mononitrotoluenes, dinitrobenzenes and dinitrotoluenes.

The process according to the invention can advantageously be carried out with a mixture of isomers.

The aromatic nitro compounds can be used in the presence of a solvent for the said aromatic nitro compounds.

According to a first variant, the solvent used is chosen from aliphatic alcohols and cyclic ethers, alone or as a mixture.

More particularly, methanol, ethanol, propanol or isopropanol is used as aliphatic alcohol, alone or as a mixture.

As cyclic ether, mention may be made of dioxane or tetrahydrofuran, alone or as a mixture.

According to this variant, prior to injection into the first reactor, the fresh aromatic nitro compounds are dissolved in the abovementioned solvent or mixture of solvents.

The concentration of nitro compounds in the solvent or mixture of solvents can vary within a wide range. However, single-phase mixtures, i.e. mixtures for which the solubility limit of the nitro compound(s) is not reached for the solvent or the mixture in question, are used. Without wishing to be limited, the concentration range is less than or equal to 25% by weight.

According to a second preferred variant of the invention, the solvent used is the reaction mixture obtained from the first reactor. If this variant is adopted, the fresh aromatic nitro compounds are supplied in the liquid or molten state.

This variant is advantageous in the sense that it does not dilute the reactants, as is the case when a solvent or a mixture of solvents is used. This contributes in particular towards conserving a high process production efficiency. Moreover, this variant dispenses with any additional step of separation of the products or of the solvent(s) used during the reaction, which involves risks of losses of hydrogenated products.

The hydrogen used is more particularly pure hydrogen. The term pure is understood to mean a gas comprising at least 99% hydrogen, and more particularly at least 99.9% hydrogen. It should be noted that it would not constitute a departure from the context of the present invention if the hydrogenation reaction was carried out with dilute hydrogen, although this does not bring any particular advantages to the reaction.

The hydrogen is supplied in the stoichiometric amount. However, the hydrogen is preferably used in excess relative to the aromatic nitro compounds.

More particularly, the hydrogen content is such that the excess relative to the stoichiometry is between 5 and 50 mol %. It should be noted that the fact that the hydrogenation reaction is carried out in the presence of an excess of hydrogen does not pose a problem of loss of this gas since it can be recycled.

The hydrogen pressure in the reactor ranges between 5 and 150 bar, preferably between 10 and 50 bar.

This gas is supplied by any means known to those skilled in the art which makes it possible to have homogeneous distribution of this gas inside the reactor.

The reaction is carried out in the presence of a hydrogenation catalyst which is conventional in this field.

Thus, a catalyst based on a metal from group VIII of the Periodic Table of the Elements, which may or may not be supported, is used.

Among the metals of group VIII, mention may be made most particularly of nickel, platinum and palladium, these metals being used alone or as a mixture.

Among the unsupported catalysts, Raney nickel is particularly suitable.

When the hydrogenation is carried out in the presence of a supported catalyst, the support can be chosen from inert materials such as kieselguhr, charcoal, alumina and silica.

In this case, the metal content is usually between 0.1 and 10% by weight, preferably between 0.3 and 5% by weight.

The catalyst is in a form which is suitable for use in a fixed bed. For example, beads, extrudates and chips are possible forms.

The objects are generally between 1 and 5 mm in size.

The figure represents a preferred embodiment of the invention, i.e. one in which the catalytic bed is immersed. The flows (1) and (2) respectively represent the hydrogen and the aromatic nitro compound, which is preferably in the molten state. The flow (1) is homogeneously distributed inside the reactor.

The flows (1) and (2) are placed in contact with the catalyst in the reactor A.

On leaving the reactor, the flow (3) is introduced into a gas-liquid separator B from which a gaseous fraction (4) mainly comprising hydrogen, and a liquid fraction (5) are separated.

According to a first embodiment, all of the flow (5) is conveyed to the exchanger C. The aim of this exchanger is to lower the temperature of the degassed reaction mixture so as to obtain the desired temperature after mixing with the nitro compounds in the flow (2).

On leaving the exchanger C, some of the flow (5a) is conveyed to the reactor D; the other part, (5b), is recycled into the foot of the reactor A.

According to a second embodiment, some of this flow (5) comes from upstream of the exchanger C. This makes it possible in particular to reduce the size of the exchanger. Thus, according to this embodiment, some of the flow referred to as (5'a) and/or some of the flow referred to as (5'b) can come from upstream of the exchanger, in order then to combine them with the flows (5a) and (5b) respectively.

The liquid fraction (5a) or (5'a) and the gaseous flow (4) feed the reactor D so as to keep the catalytic bed immersed. The reaction mixture (6) is introduced into a separator and the gaseous fraction (7), mainly comprising hydrogen, can advantageously be recycled upstream in the process, for example into the supply of the reactor A. The liquid fraction (8) comprising the water and the hydrogenated aromatic compounds are processed in order to remove the water.

The hydrogenated compounds can be used in particular for the preparation of isocyanates, which are polyurethane intermediates.

The example which follows illustrates the invention without limiting it.

EXAMPLE

The hydrogenation reaction is carried out in apparatus whose fittings correspond to those of the figure.

Reactor A corresponds to a tube 45 mm in diameter and 800 mm in height.

Reactor D corresponds to a tube 15 mm in diameter and 500 mm in height.

Reactor A comprises 643 g of a Pd/C catalyst comprising 0.5% by weight of palladium, in the form of chips with an average size of about 3 mm.

Reactor D comprises 50 g of the same catalyst as above.

Industrial dinitrotoluene comprising 96% of a mixture of 2,4- and 2,6-isomers in a 4:1 ratio and 4% of 3,5-/3,4-/2,5-isomers are introduced at a flow rate of 245 g/h.

The hydrogen flow rate is 580 Nl/h.

The pressure in the reactor is 25 bar.

The inlet temperature in this reactor is 80° C. and the outlet temperature is 100° C.

A flow rate of 20 l/h of degassed reaction mixture cooled in order to obtain a temperature in the region of 80° C. is recycled into the reactor A.

In this reactor, the degree of conversion of the dinitrotoluene supplied is greater than 95%.

Reactor D is fed such that the volume in the first reactor remains constant.

The pressure in reactor D is identical and the inlet temperature is 80° C.

On leaving this second reactor, the degree of conversion of the dinitrotoluenes is total and the selectivity is greater than 98%.

What is claimed is:

1. A process for hydrogenating aromatic nitro compounds through a hydrogenation reaction, comprising the steps of:
   a) reacting at least one aromatic nitro compound With hydrogen in two fixed-bed catalytic reactors in series and comprising a first reactor and a second reactor operating adiabatically to obtain a reaction mixture;
   b) recycling a part of the reaction mixture leaving the first reactor into this first reactor, and introducing the other part into the second reactor; and
   c) supplying each of the reactors with hydrogen, at least one aromatic nitro compound, or the recycled or non-recycled reaction mixture, co-currentwise, in order to obtain a continuous liquid phase in said reactors.

2. A process for hydrogenating aromatic nitro compounds through a hydrogenation reaction, comprising the steps of:
   a) reacting at least one aromatic nitro compound with hydrogen in two fixed-bed catalytic reactors in series comprising a first reactor and a second reactor operating adiabatically to obtain a reaction mixture;
   b) recycling a part of the reaction mixture leaving the first reactor into this first reactor, and introducing the other part into the second reactor; and
   c) supplying each of the reactors with hydrogen, at least one nitro compound, and the recycled or non-recycled reaction mixture, co-currentwise, in order to obtain a continuous liquid phase in said reactors.

3. A process according to claim 1, wherein the aromatic nitro compounds present a concentration of between 0.1 and 10% by weight in the first reactor.

4. A process according to claim 1, further comprising the step of carrying out the reaction with the reaction mixture having an outlet temperature and the aromatic nitro compounds or the recycled reaction mixture having an inlet temperature, the difference between said outlet and said inlet temperature being less than 120° C.

5. A process according to claim 1, further comprising the step of separating gases from the reaction mixture leaving the first reactor before recycling into this first reactor and before introduction into the second reactor.

6. A process according to claim 1, wherein said aromatic nitro compounds present at least one nitro group.

7. A process according to claim 1, further comprising the step of carrying out the reaction in the presence of a solvent for said aromatic nitro compounds.

8. A process according to claim 7, wherein the solvent is an aliphatic alcohol or a cyclic ether.

9. A process according to claim 1, further comprising the step of carrying out the reaction in the presence of an excess of hydrogen, relative to the stoichiometry, of 5 to 50 mol %.

10. A process according to claim 1, further comprising the step of carrying out the reaction in the presence of a catalyst comprising at least one metal from group VIII, optionally supported.

11. A process according to claim 2, wherein the aromatic nitro compounds present a concentration of between 0.1 and 10% by weight in the first reactor.

12. A process according to claim 2, further comprising the step of carrying out the reaction with the reaction mixture having an outlet temperature and the aromatic nitro compounds and the recycled reaction mixture having an inlet temperature, the difference between said outlet and said inlet temperature being less than 120° C.

13. A process according to claim 2, further comprising the step of separating gases from the reaction mixture leaving the first reactor before recycling into this first reactor and before introduction into the second reactor.

14. A process according to claim 2, wherein said aromatic nitro compounds present at least one nitro group.

15. A process according to claim 2, further comprising the step of carrying out the reaction in the presence of a solvent for said aromatic nitro compounds.

16. A process according to claim 15, wherein the solvent is an aliphatic alcohol or a cyclic ether.

17. A process according to claim 2, further comprising the step of carrying out the reaction in the presence of an excess of hydrogen, relative to the stoichiometry, of 5 to 50 mol %.

18. A process according to claim 2, further comprising the step of carrying out the reaction in the presence of a catalyst comprising at least one metal from group VIII, optionally supported.

19. A process according to claim 7, wherein the solvent is the reaction mixture.

20. A process according to claim 1, wherein the first reactor has a foot having a temperature of about 50 to about 200° C.

21. A process according to claim 19, wherein the temperature is of about 80 to about 170° C.

* * * * *